(12) United States Patent
Glass et al.

(10) Patent No.: US 7,146,206 B2
(45) Date of Patent: Dec. 5, 2006

(54) DETECTION OF CARDIAC ARRHYTHMIA USING MATHEMATICAL REPRESENTATION OF STANDARD ΔRR PROBABILITY DENSITY HISTOGRAMS

(75) Inventors: Leon Glass, Montreal (CA); Katsumi Tateno, Kitakyushu (JP)

(73) Assignee: Medtronic, Inc., Minneapolis, MN (US)

( * ) Notice: Subject to any disclaimer, the term of this patent is extended or adjusted under 35 U.S.C. 154(b) by 511 days.

(21) Appl. No.: 10/382,385

(22) Filed: Mar. 6, 2003

(65) Prior Publication Data

US 2005/0004486 A1  Jan. 6, 2005

Related U.S. Application Data

(60) Provisional application No. 60/365,623, filed on Mar. 20, 2002.

(51) Int. Cl.
*A61B 5/04* (2006.01)
(52) U.S. Cl. ........................ 600/521; 600/509
(58) Field of Classification Search ................ 600/521, 600/515, 516, 517, 518, 519
See application file for complete search history.

(56) References Cited

U.S. PATENT DOCUMENTS

| | | | | |
|---|---|---|---|---|
| 3,820,025 A | * | 6/1974 | Lahr et al. | 368/114 |
| 3,880,147 A | * | 4/1975 | Gruenke et al. | 600/515 |
| 4,000,461 A | * | 12/1976 | Barber et al. | 600/521 |
| 4,202,340 A | * | 5/1980 | Langer et al. | 607/5 |
| 4,240,442 A | * | 12/1980 | Andresen et al. | 600/521 |
| 4,417,306 A | * | 11/1983 | Citron et al. | 600/521 |

(Continued)

FOREIGN PATENT DOCUMENTS

WO    WO 02/24068 A1    3/2002

OTHER PUBLICATIONS

Tateno, K., "Automatic Detection of Atrial Fibrillation Using the Coefficient of Variation and Density Histograms of RR and ΔRR Intervals", *Medical & Biological Engineering & Computing*, 2001, vol. 39, pp. 664-671.

(Continued)

*Primary Examiner*—Robert E. Pezzuto
*Assistant Examiner*—Brian T. Gedeon
(74) *Attorney, Agent, or Firm*—Paul H. McDowall; Michael C. Soldner; Girma Wolde-Michael

(57) ABSTRACT

A method and a system for detecting cardiac arrhythmias that includes detecting RR intervals of the patient wherein each RR interval is an interval between two heart beats, and simulating standard probability density histograms of ΔRRs by means of a suitable probability distribution calculated through at least one mathematical formulae, wherein ΔRR is a difference between two successive RR intervals. Test probability density histograms of ΔRRs of the patient are constructed from the detected RR intervals. Finally, the standard and test histograms are compared to detect whether the patient suffers from cardiac arrhythmia. As non limiting examples, the standard probability density histograms of ΔRRs are modeled by a mathematical equation selected from the group consisting of: the Lorentzian distribution, the Gaussian distribution, the Student's t-distribution, and a probability distribution including a linear combination of the Lorentzian and Gaussian distribution.

3 Claims, 13 Drawing Sheets

U.S. PATENT DOCUMENTS

| | | |
|---|---|---|
| 5,330,508 A | 7/1994 | Gunderson |
| 5,509,425 A * | 4/1996 | Feng .......................... 600/515 |
| 5,591,215 A | 1/1997 | Greenhut et al. |
| 5,603,331 A | 2/1997 | Heemels et al. |
| 5,730,142 A * | 3/1998 | Sun et al. ................... 600/578 |
| 5,749,900 A | 5/1998 | Schroeppel et al. |
| 5,772,604 A | 6/1998 | Langberg et al. |
| 5,778,881 A * | 7/1998 | Sun et al. ................... 600/509 |
| 5,782,888 A * | 7/1998 | Sun et al. ..................... 607/27 |
| 5,941,831 A | 8/1999 | Turcott |
| 5,951,592 A | 9/1999 | Murphy |
| 6,035,233 A | 3/2000 | Schroeppel et al. |
| 6,061,592 A | 5/2000 | Nigam |
| 6,064,906 A | 5/2000 | Langberg et al. |
| 6,144,878 A | 11/2000 | Schroeppel et al. |
| 6,233,487 B1 * | 5/2001 | Mika et al. ................... 607/27 |
| 6,480,734 B1 * | 11/2002 | Zhang et al. ............... 600/518 |
| 6,804,551 B1 * | 10/2004 | Griffin et al. ............... 600/515 |

OTHER PUBLICATIONS

Murgatroyd, et al., "Identification of Atrial Fibrillation Episodes in Ambulatory Electrocardiographic Recordings: Validation of a Method for Obtaining Labeled R—R Interval Files", *PACE,* vol. 18., Jun. 1995, pp. 1315-1320.

Slocum, et a., "Computer Detection of Atrial Fibrillation on the Surface Electrocardiogram", *IEEE,* 1987, pp. 253-254.

Moody, et al., "A New Method for Detecting Atrial Fibrillation Using R—R Intervals", *IEEE,* 1983, pp. 227-230.

Bottsma, et al., "Analysis of R—R Intervals in Patients with Atrial Fibrillation at Rest and During Exercise", *Circulation,* vol. XLI, May 1970, pp. 783-794.

Pinciroli, et al., "Pre-Clinical Experimentation Of A Quantitative Synthesis of the Local Variability in the Original R—R Interval Sequence in the Presence of Arrythmia", *Automedica,* 1986, vol. 6, pp. 295-317.

* cited by examiner

FIG_1

FIG_2

(a) 400 – 449 ms
(b) 750 – 799 ms
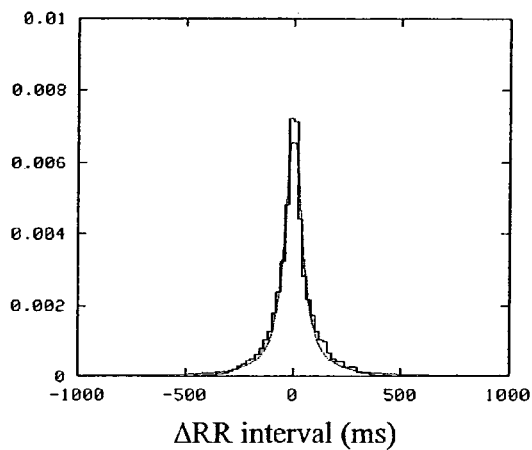
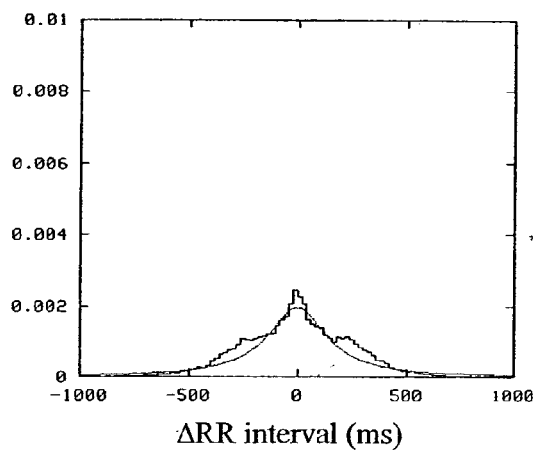
(c) 1000 – 1049 ms
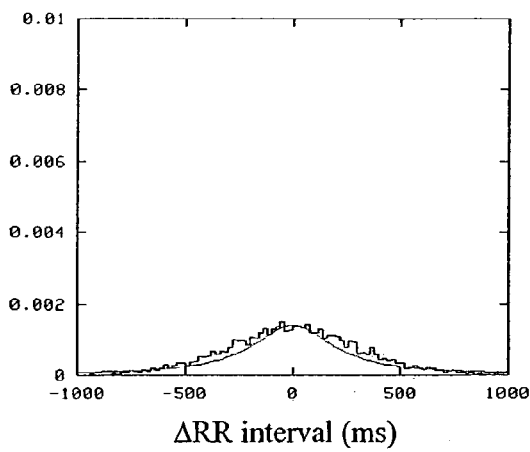
Figure 4

(a) 400 – 449 ms
(b) 750 – 799 ms
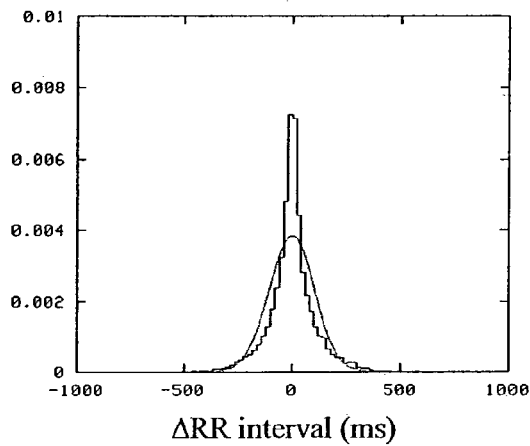
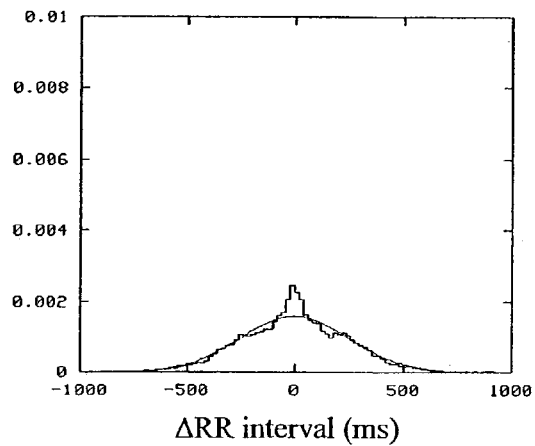
(c) 1000 – 1049 ms
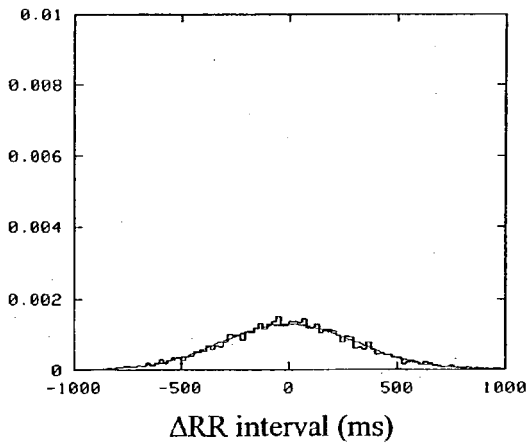
Figure 5

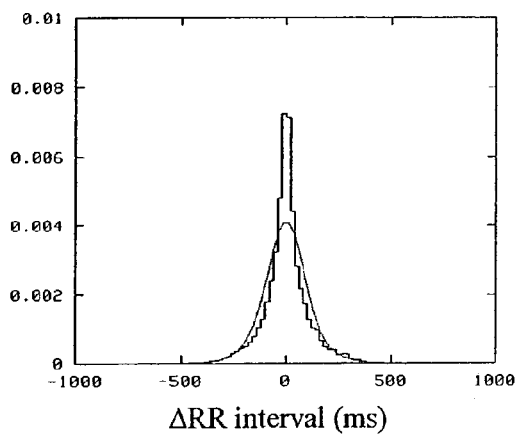
(a) 400 – 449 ms
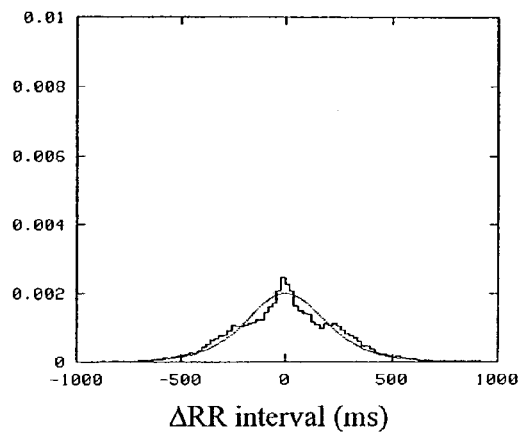
(b) 750 – 799 ms
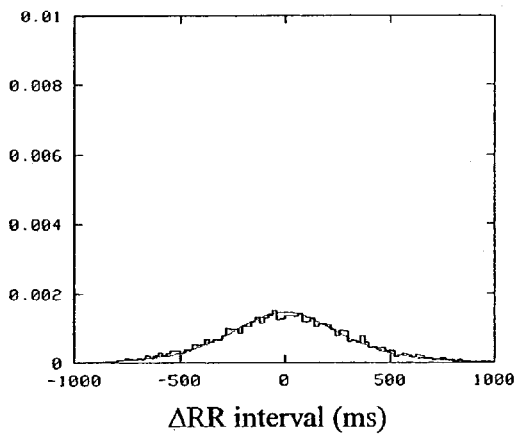
(c) 1000 – 1049 ms
Figure 6

(a) 400 – 449 ms
(b) 750 – 799 ms
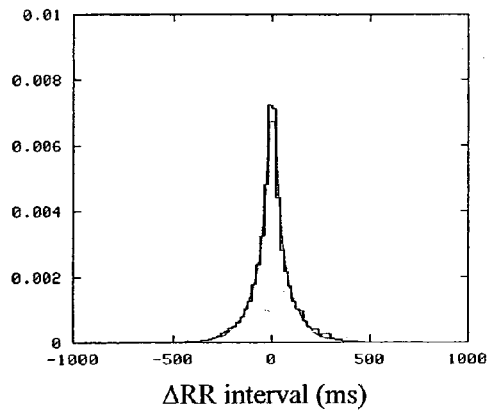
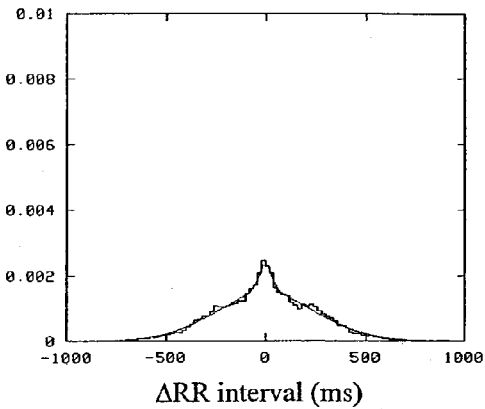
(c) 1000 – 1049 ms
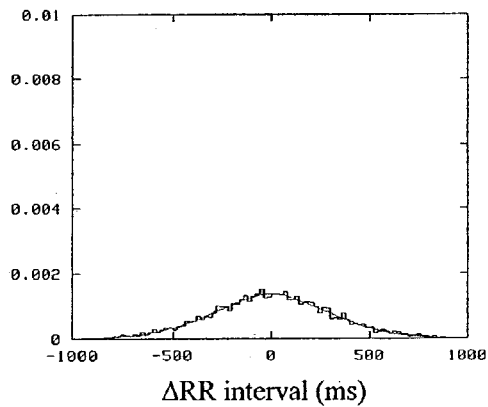
(d)
(e)
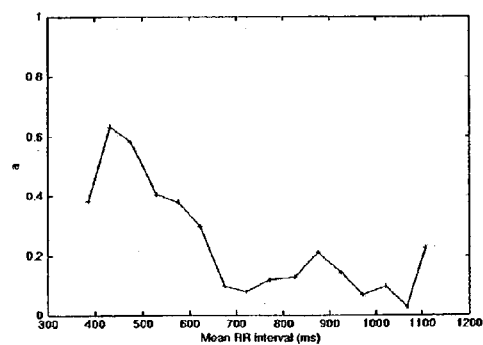
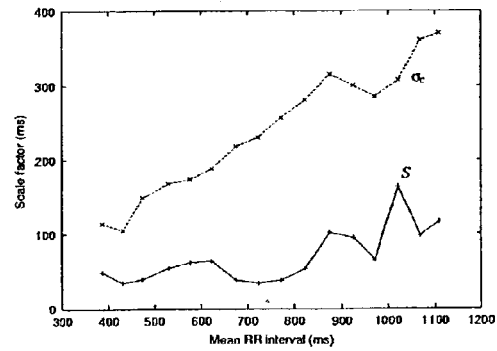
Figure 7

DETECTION OF CARDIAC ARRHYTHMIA USING MATHEMATICAL REPRESENTATION OF STANDARD ΔRR PROBABILITY DENSITY HISTOGRAMS

RELATED APPLICATION

This application claims priority and other benefits from U.S. Provisional Patent Application Ser. No. 60/365,623, filed Mar. 20, 2002, entitled "MATHEMATICAL REPRESENTATION OF STANDARD ΔRR PROBABILITY DENSITY HISTOGRAMS", incorporated herein by reference in its entirety.

FIELD OF THE INVENTION

The present invention relates to a method and a system for detecting cardiac arrhythmias from internally and/or externally detected activity of the heart by means of ΔRR intervals wherein the standard ΔRR probability density histograms are fitted by a mathematical distribution.

BRIEF DESCRIPTION OF THE CURRENT TECHNOLOGY

Atrial fibrillation is a common and serious cardiac arrhythmia that is characterized by rapid, irregular atrial activation and is known to be associated with life threatening sequelae such as stroke. The atrial activations are irregularly transmitted through the atrioventricular node leading to a correspondingly irregular sequence of ventricular activations as monitored by the ventricular interbeat (RR) intervals on the surface electrocardiogram (ECG). An RR interval is an interval between two successive heart beats. Clinically, in the surface ECG, atrial fibrillation is diagnosed by absence of P waves (normally associated with the near synchronous activation of the atria) and a rapid irregular ventricular rate. P waves are difficult to determine automatically and irregular baseline activity of the ECG is common in atrial fibrillation.

Although a number of different methods have been proposed to test for atrial fibrillation based on assessment of the RR intervals and/or the surface ECG, the detection of atrial fibrillation based on this data nevertheless poses substantial problems [Murgatroyd, et al. "*Identification of Atrial Fibrillation Episodes in Ambulatory Electrocardiographic Recordings: Validation of a Method for Obtaining Labeled R-R Interval Files,*" Pacing and Clinical Electrophysiology, (1995), pp. 1315–1320]. In the following description, the main strategies that have been proposed to assess atrial fibrillation based on knowledge of the RR intervals and/or ECG will be briefly reviewed.

Since RR intervals during atrial fibrillation have a larger standard deviation and a more rapid decay of the autocorrelation function, there are proposals that the standard deviation and the autocorrelation function can be used to distinguish atrial fibrillation from sinus rhythm [Bootsma, et al. "*Analysis of RR Intervals in Patients with Atrial Fibrillation at Rest and During Exercise,*" Circulation, (1970), pp. 783–794]. Since other abnormal rhythms also have a large standard deviation of RR intervals and a rapid decay of the autocorrelation function, these methods are difficult to apply in concrete situations.

Moody and Mark [G. Moody, et al. "*A New Method for Detecting Atrial Fibrillation Using R-R Intervals,*" Computers in Cardiology, (1983), pp. 227–230] classify RR intervals as short, long or regular. They then construct a Markov model for the probabilities for transitions between RR intervals in each of the three different length classes. Atrial fibrillation data has typical transition probabilities not shared by normal rhythms or other arrhythmia. Although the Markov model has high sensitivity for detecting atrial fibrillation, it tends to have a relatively low predictive value of a positive test.

Pinciroli and Castelli have investigated the morphology of histograms of RR intervals collected during atrial fibrillation and other arrhythmia [F Pinciroli, et al. "*Pre-clinical Experimentation of a Quantitative Synthesis of the Local Variability in the Original R-R Interval Sequence in the Presence of Arrhythmia,*" Automedica, (1986), vol. 6, pp. 295–317. Pinciroli and Castelli, 1986]. They demonstrated that the histograms of the ratio between successive RR intervals show characteristic differences between normal rhythm and atrial fibrillation. The histogram of the ratio between successive RR intervals is symmetrical to the mean value. No quantitative methods were proposed to quantify the symmetry or to use it to develop a quantitative test.

Since the baseline of the ECG is irregular during atrial fibrillation, Slocum [J. Slocum, et al. "*Computer Detection of Atrial Fibrillation on the Surface Electrocardiogram,*" Computers in Cardiology, (1987), pp. 253–254] has proposed that the regularity of the baseline, as determined by the power spectrum of the residual ECG after subtraction of the baseline of the QRS complexes can be used to detect atrial fibrillation. This method is necessarily sensitive to small amounts of noise that might corrupt the baseline of the ECG.

Implantable ventricular and atrial defibrillators are devices that distinguish atrial and ventricular fibrillation from other rhythms. Typically, electrodes in these devices record intracardiac activity directly from the atria and ventricles. The methods that are used to detect atrial fibrillation in these devices cannot be easily applied to recordings that give information about the timing of the QRS complexes (U.S. Pat. No. 6,144,878, issued to Schroeppel on Nov. 7, 2000; U.S. Pat. No. 6,035,233 issued to Schroeppel on Mar. 7, 2000; U.S. Pat. No. 5,749,900 issued to Schroeppel on May 24, 1998; U.S. Pat. No. 6,064,906 issued to Langberg et al. on May 16, 2000; U.S. Pat. No. 5,772,604 issued to Langberg et al. on Jun. 30, 1998; U.S. Pat. No. 6,061,592 issued to Nigam on May 9, 2000; U.S. Pat. No. 5,951,592 issued to Murphy on Sep. 14, 1999; U.S. Pat. No. 5,941,831 issued to Turcott on Aug. 24, 1999; U.S. Pat. No. 5,591,215 issued to Greenhut et al. on Jan. 7, 1997).

Analysis of a histogram of the interbeat intervals can be used to discriminate between ventricular fibrillation and ventricular tachycardia. By counting the number of beats in predetermined interval classes, an algorithm identifies a given sequence as ventricular fibrillation or ventricular tachycardia (U.S. Pat. No. 5,330,508 issued to Gunderson on Jul. 19, 1994). While the foregoing patent suggests that the invention is of value in detecting and treating atrial fibrillation (column 2, lines 29–31), it does not provide a specific embodiment for detecting and treating atrial fibrillation.

Based on the foregoing review, it is apparent that there is a need for a method and a system for determining whether or not a given recording constitutes atrial fibrillation based on the timing of the QRS complexes as measured from an internal and/or external monitor. Assessment of whether a patient is in atrial fibrillation based on the timing of the QRS complexes would be extremely useful, for example, for assessing the efficacy of specific drugs of a patient fitted with a monitoring device that measures the timing of the QRS complexes.

It was shown previously that atrial fibrillation could be reliably detected and quantitated from the surface electrocardiogram based on the density histograms of the ☐RR collected during atrial fibrillation, where RRRARR is defined as the difference between two successive RR intervals. Using the Kolmorogov-Smirnov test based on ΔRR resulted in high sensitivity and specificity in the MIT-BIH atrial fibrillation database. However, there remains a need to increase the accuracy of detection of atrial fibrillation using the Kolmorogov-Smirnov test based on ΔRR. There is also a need to obtain rapid results that can be achieved by reducing the data storage load -and -computation time.

SUMMARY OF THE INVENTION

To increase the accuracy of detection and reduce the storage requirements for the standard density histograms and therefore the computational load related to detection of atrial fibrillation or other cardiac arrhythmias, there is provided, in accordance with the present invention a method for detecting cardiac arrhythmia of a patient, comprising:

detecting RR intervals of the patient wherein each RR interval is an interval between two heart beats;

constructing standard probability density histograms of ΔRRs collected during cardiac arrhythmia of a plurality of subjects, wherein ☐RR is a difference between two successive RR intervals;

modeling the standard probability density histograms of ΔRRs by means of a suitable probability distribution calculated through at least one mathematical formulae;

constructing test probability density histograms of ΔRRs of the patient from the detected RR intervals of this patient; and comparing the standard modeled histograms and the test histograms to detect whether the patient suffers from cardiac arrhythmia.

The present invention also relates to a system for detecting cardiac arrhythmia such as atrial fibrillation in a patient, comprising:

a detector of RR intervals of the patient, wherein each RR interval is an interval between two heart beats;

a standard probability density histogram storage unit in which are stored standard probability density histograms of ΔRRs collected during cardiac arrhythmia of a plurality of subjects, these standard probability density histograms of ΔRRs being modeled by means of a suitable probability distribution calculated through at least one mathematical formulae, and ΔRR being the difference between two successive RR intervals;

a test ΔRR histogram calculator supplied with the detected RR intervals from the detector and constructing test histograms of the ΔRRs of the patient; and a standard and test ΔRR histograms comparator supplied with the standard modeled probability density histograms and test histograms, this comparator comprising a detector of cardiac arrhythmia of the patient responsive to the comparison of the standard and test histograms.

As non limiting examples, the standard probability density histograms of ΔRRs are modeled by a mathematical equation selected from the group consisting of: the Lorentzian distribution, the Gaussian distribution, the Student's t-distribution, and a probability distribution comprising a linear combination of the Lorentzian and Gaussian distribution.

It is within the scope of the present invention to apply the above concept to detection of not only atrial fibrillation but also to other cardiac arrhythmias including in particular but not exclusively atrial flutter, multifocal atrial tachycardia, ventricular tachycardia, premature ventricular contractions, etc., as well as to detection of other body phenomenon involving electrical activity.

The foregoing and other objects, advantages and features of the present invention will become more apparent upon reading of the following non restrictive description of illustrative embodiments thereof, given by way of example only with reference to the accompanying drawings.

BRIEF DESCRIPTION OF THE DRAWINGS

In the appended drawings:

FIG. 4 are curves comparing three sets of standard ΔRR probability density (solid line) histograms (mean RR intervals 400–449 ms; 750–799 ms; and 1000–1049 ms) to the Lorentzian distribution (dotted line).

FIG. 5 are curves comparing three sets of standard ΔRR probability density (solid line) histograms (mean RR intervals 400–449 ms; 750–799 ms;

and 1000–1049 ms) to the Gaussian distribution (dotted line).

FIG. 6 are curves comparing three sets of standard ΔRR probability density (solid line) histograms (mean RR intervals 400–449 ms; 750–799 ms; and 1000–1049 ms) to the Student's t-distribution (dotted line).

FIG. 7 are curves comparing three sets of standard ΔRR probability density (solid line) histograms (mean RR intervals 400–449 ms; 750–799 ms; and 1000–1049 ms) to a linear combination of the Lorentzian distribution and the Gaussian distribution (dotted line).

Figure 8:
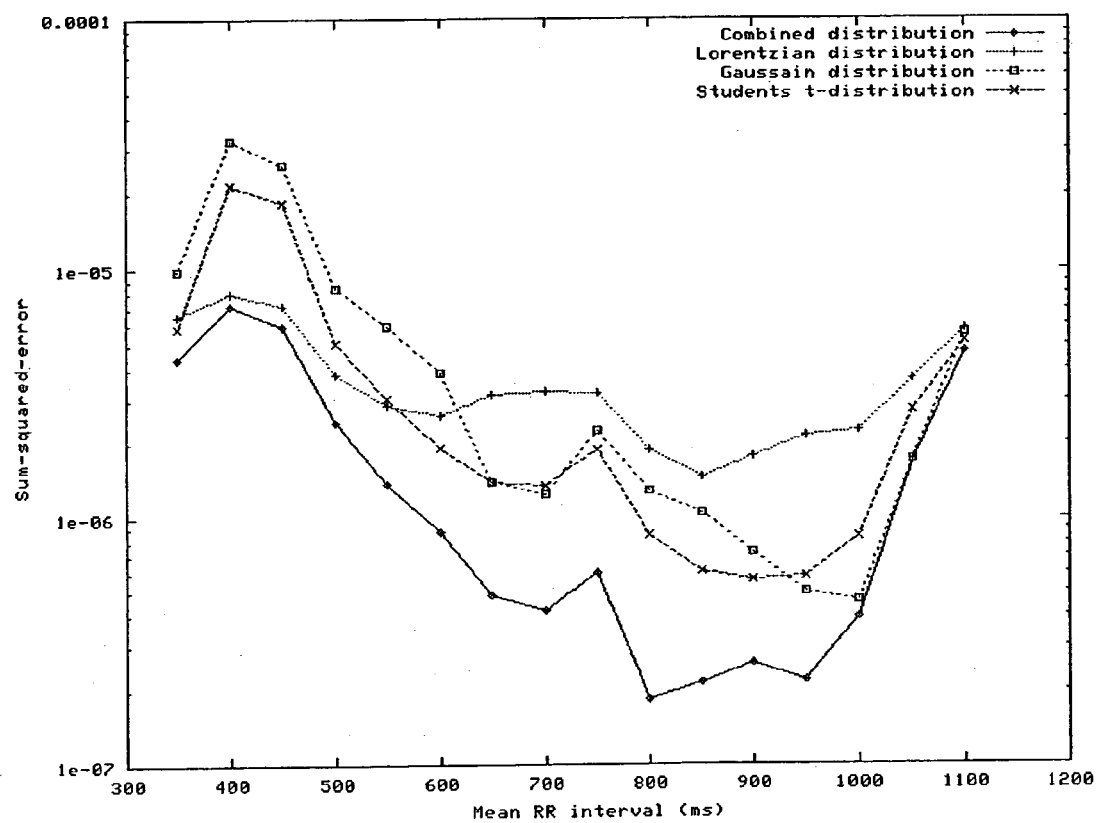

FIG. 8 illustrates the fidelity (squared error $\epsilon^2$) of curve fitting for the four mathematical representations of probability distributions versus empirical distributions of standard density histograms as a function of mean RR intervals (ms).

Figure 3:
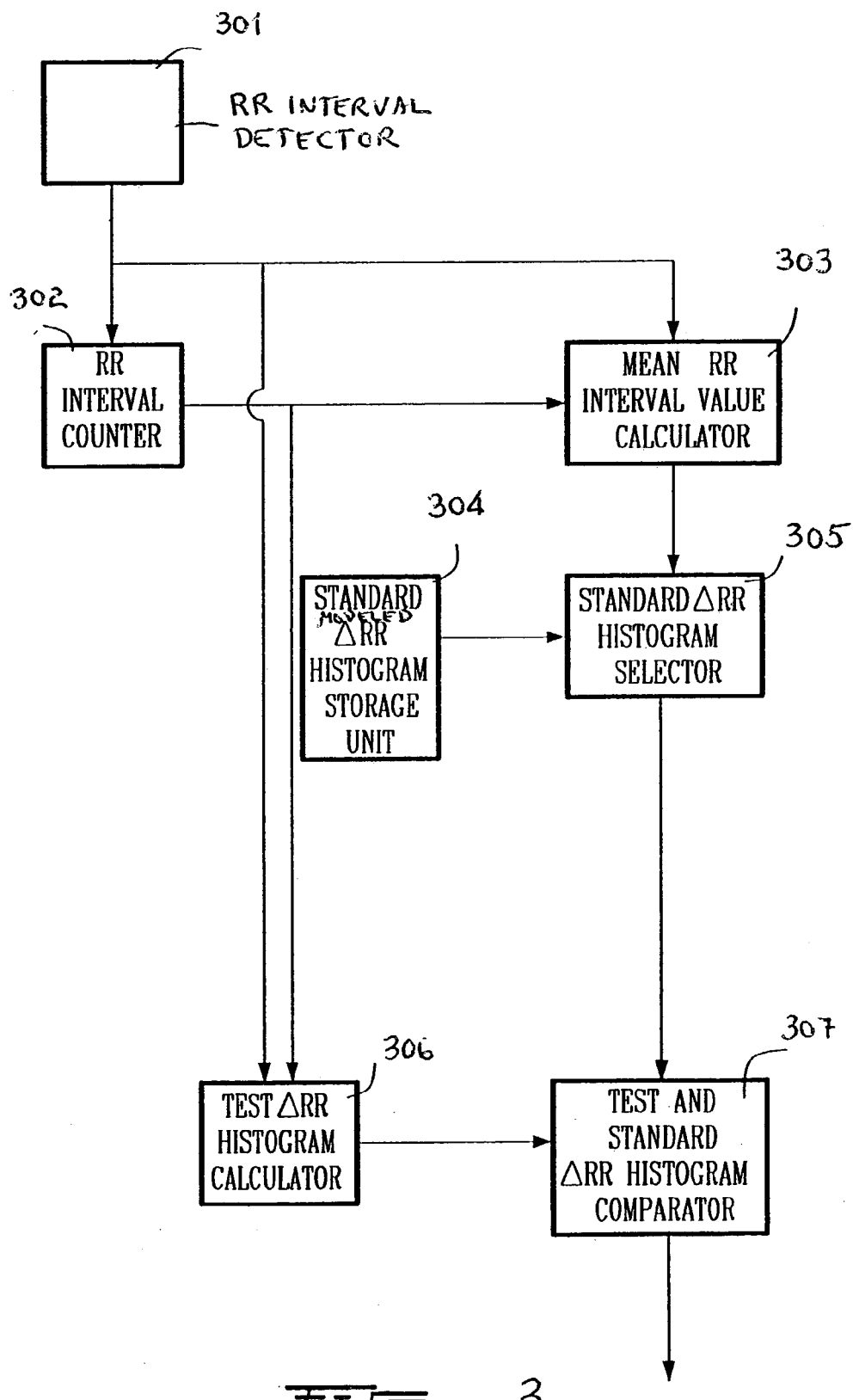
FIG. 3 is a block diagram of an illustrative embodiment of the system according to the present invention for implementing the method of FIG. 2, for detecting atrial fibrillation based on RR intervals.
Figure 9:
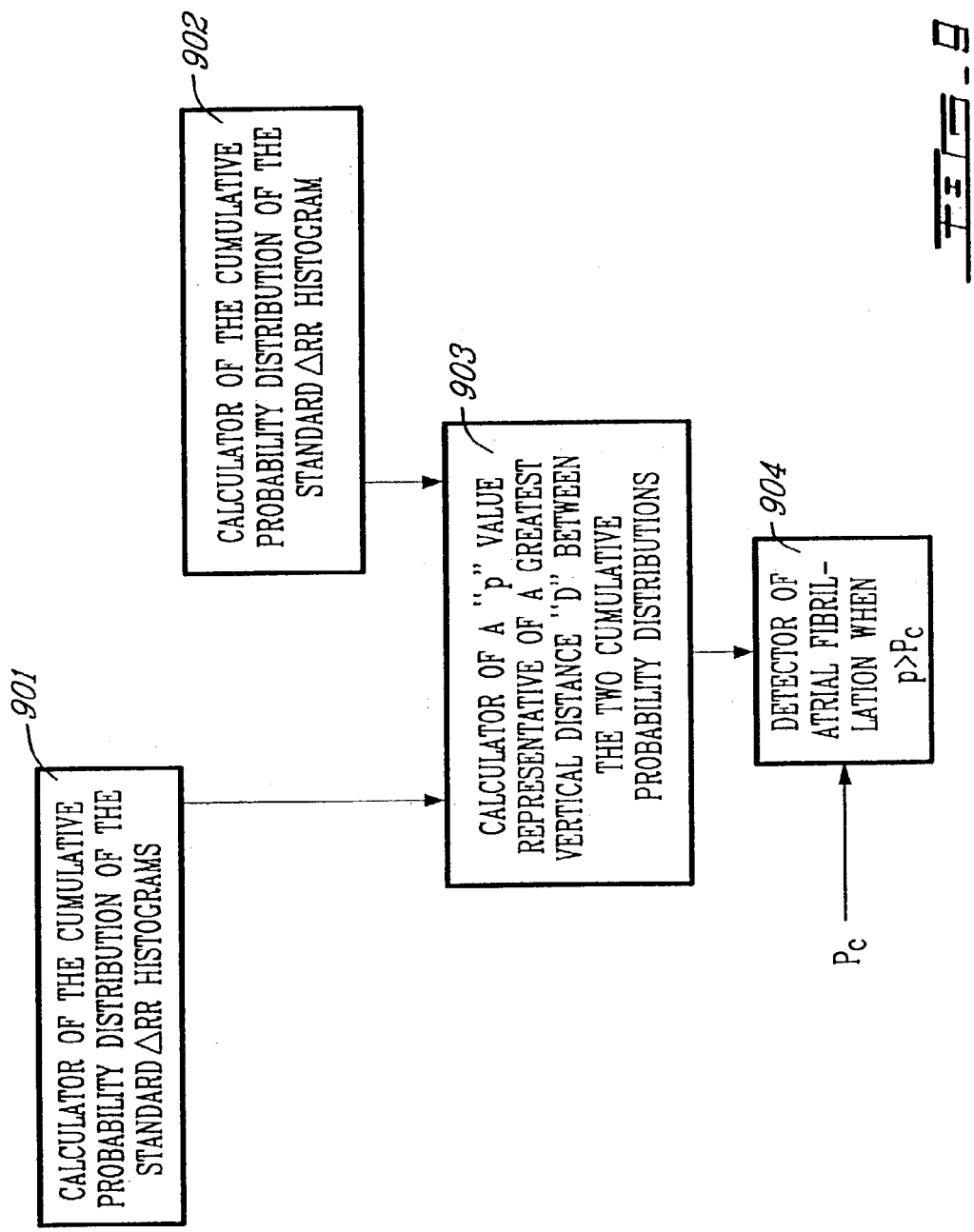

FIG. 9 is a block diagram of an illustrative embodiment of a test and standard ΔRR histogram comparator forming part of the system of FIG. 3.

Figure 10:
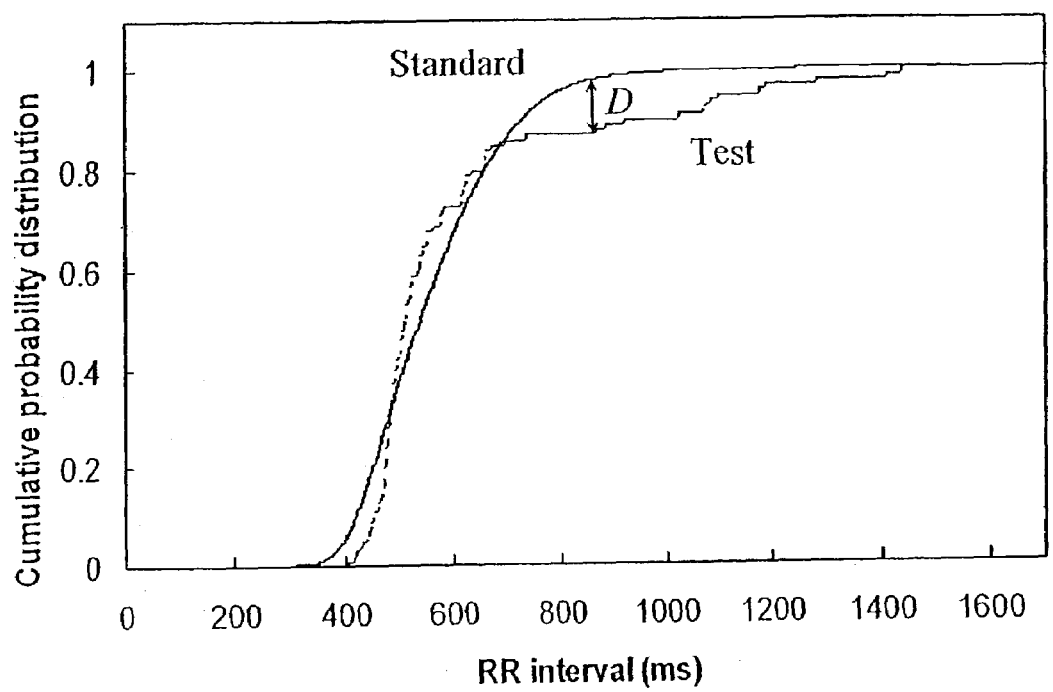

FIG. 10 is a curve illustrating the Kolmogorov-Smirnov (KS) test. A cumulative probability distribution based on patient test data is compared with a standard cumulative probability distribution. D is the greatest distance between two cumulative probability distributions.

Figure 11:
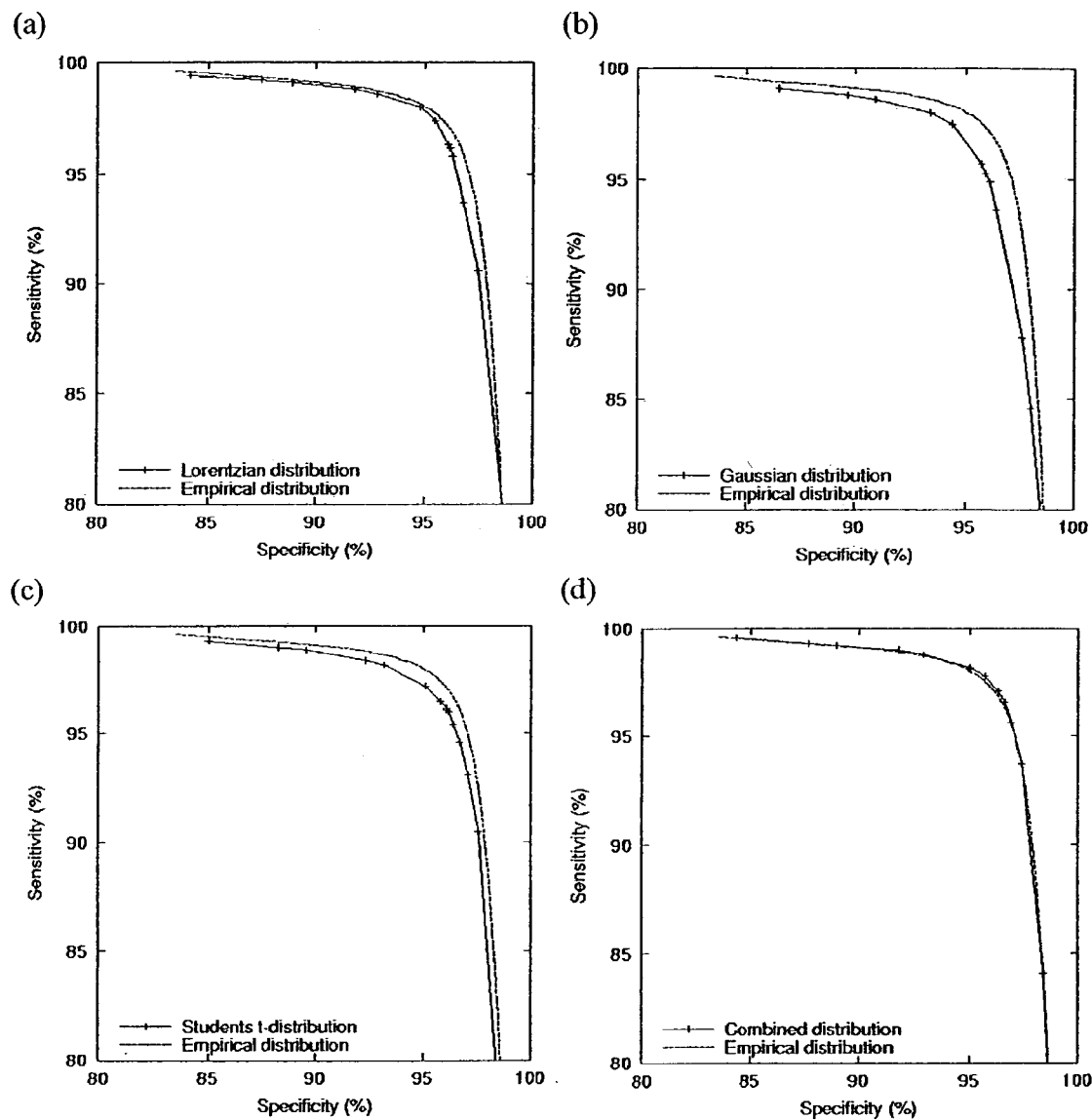

FIG. 11 shows curves illustrating the Receiver Operating Characteristic curve (ROC) of the Kolmogorov-Smirnov test when applied to the MIT-BIH atrial fibrillation/flutter database using the: (a) Lorentzian distribution; (b) Gaussian distribution; (c) Student's t-distribution; and (d) Combined probability distribution. The respective ROCs are compared to the ROCs derived from the standard density histograms.

Figure 12:
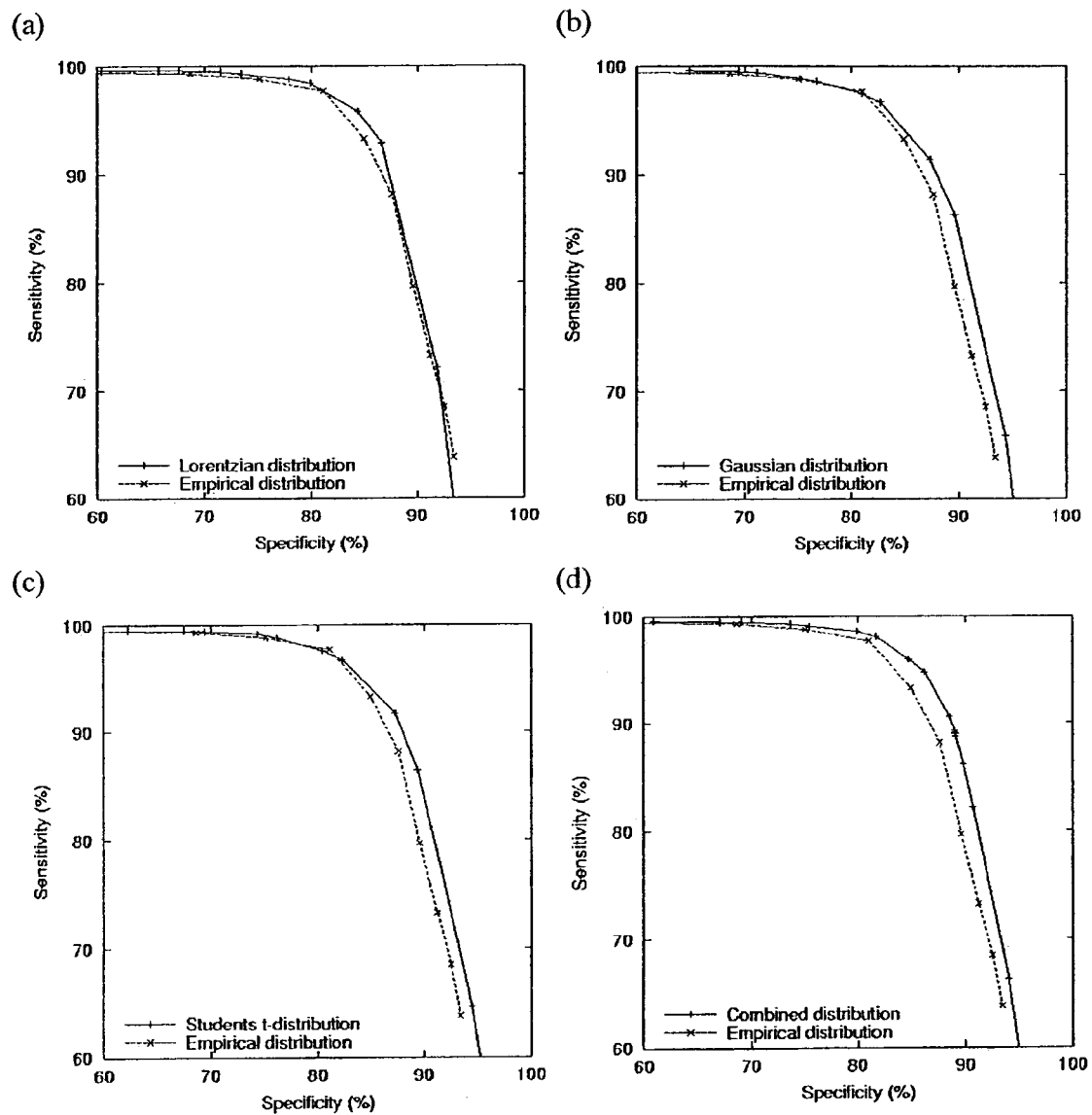

FIG. 12 shows curves illustrating the receiver operating characteristic curve (ROC) of the Kolmogorov-Smirnov test when applied to the 200 series MIT-BIH arrhythmia database using the: (a) Lorentzian distribution (b) Gaussian distribution (c) Student's t-distribution and (d) Combined probability distribution. The respective ROCs are compared to the ROCs derived from the standard density histograms.

Figure 13:
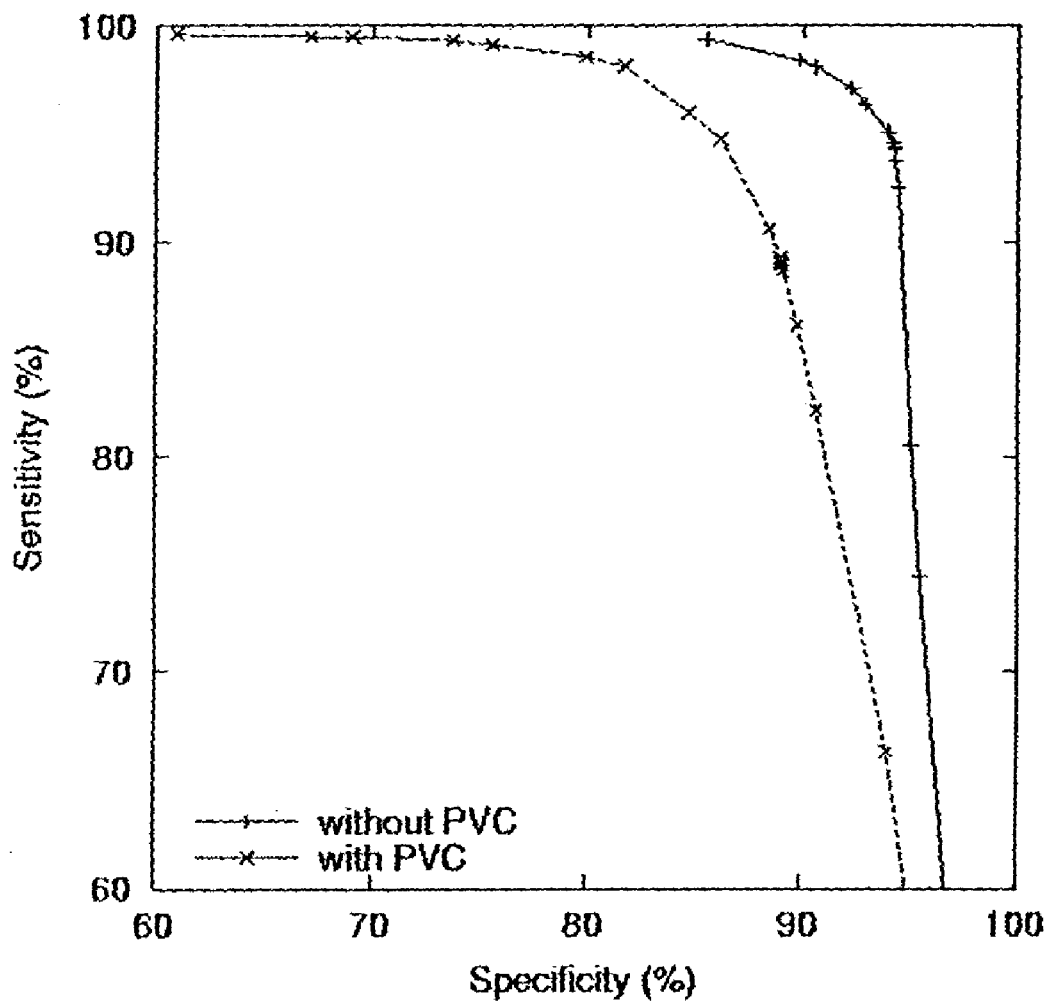

FIG. 13 is a curve illustrating the ROC related to the Kolmogorov-Smirnov test using the combined Lorentzian and Gaussian probability distributions and the 200 series of the MIT-BIH arrhythmia database from which premature ventricular contractions are eliminated.

DETAILED DESCRIPTION OF THE ILLUSTRATIVE EMBODIMENTS

Although the illustrative embodiments of the present invention will be described in relation to atrial fibrillation, it may be appreciated that the same concepts can be applied to detection of other cardiac arrhythmias including in particular but not exclusively atrial flutter, multifocal atrial tachycardia, ventricular tachycardia, premature ventricular contractions, etc. This concept can also be applied to detection of other body phenomenon involving electrical activity.

Data was obtained from the MIT-BIH atrial fibrillation/flutter database and the MIT-BIH arrhythmia database. The atrial fibrillation database contains 300 atrial fibrillation episodes, sampled at 250 Hz for 10 hours from Holter tapes of 25 subjects. Arrhythmia detection was carried out by trained observers and was confirmed by an independent evaluation. The timing of each QRS complex was determined by an automatic detector. The MIT-BIH arrhythmia database includes two categories (the 100 series and the 200 series) and contains 48 subjects. The 100 series includes normal sinus rhythm, paced rhythm, bigeminy, trigeminy and supraventricular tachycardia, but it does not contain atrial fibrillation. The 200 series includes eight atrial fibrillation subjects as well as atrial bigeminy, atrial flutter, supraventricular tachyarrhythmia, ventricular flutter and ventricular tachycardia.

Figure 1:
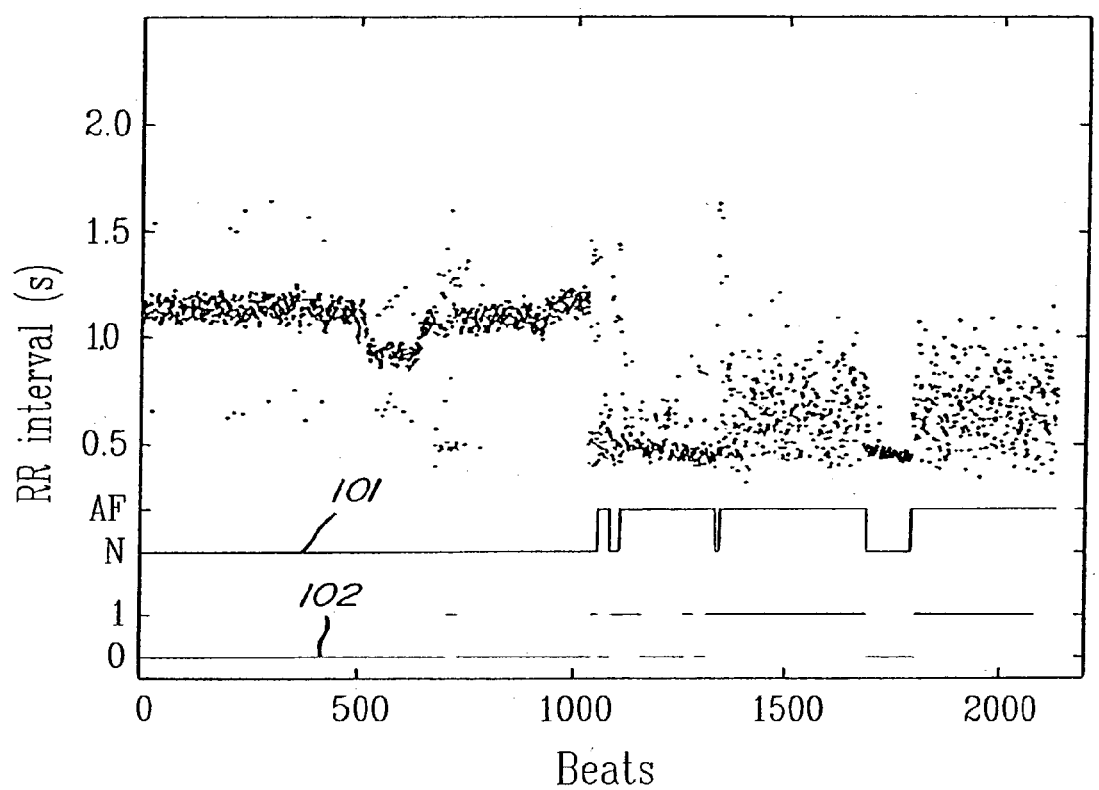
FIG. 1 is a time series showing the RR intervals from subject 202 from the MIT-BIH arrhythmia database. The solid line directly under the time series of RR intervals shows the assessment of atrial fibrillation (indicated by AF) or non-atrial fibrillation (indicated by N) as reported in the database. The solid line at the bottom of FIG. 1 indicates the assessment of atrial fibrillation, indicated by 1, and non-atrial fibrillation, indicated by 0, based on an algorithm presented herein.

FIG. 1 is a typical time series of RR intervals from a patient with atrial fibrillation. Immediately under the recording is a solid marker line 101. When atrial fibrillation occurs this marker line 101 is set to AF; otherwise it is set to N, which indicates a rhythm that is not atrial fibrillation. The graph of FIG. 1 also shows a lower solid line 102 indicating the assessment of atrial fibrillation, indicated by 1, and non-atrial fibrillation, indicated by 0, based on an algorithm according to the present invention. At the onset of atrial fibrillation, the rhythm dramatically changes to irregular with large fluctuation. In paroxysmal atrial fibrillation there is sudden starting and stopping of atrial fibrillation.

The standard ΔRR probability density histograms are prepared as described hereinafter before the detection of atrial fibrillation.

RR intervals of the patient are first detected (201 of FIG. 2) through an internal and/or external RR interval detector 301 (FIG. 3) detecting electrical activity of the heart beat of the patient.

ΔRR is defined as the difference between two successive RR intervals. In the illustrative embodiment, blocks of 100 successive beats or RR intervals are processed during atrial fibrillation. For that purpose, the detected RR intervals from the detector 801 are counted (202 of FIG. 2) by a RR interval counter 302 (FIG. 3) until the number of detected RR intervals reaches 100 intervals (203 of FIG. 2).

The mean value of each block of 100 RR intervals is computed (204 of FIG. 2) by means of a calculator 303 from the RR intervals from the detector 301. Of course, the calculator 303 is supplied with the count from the counter 302. This mean value identifies the block of 100 RR intervals as falling into one of sixteen (16) different classes, respectively corresponding to mean values of RR between 350–399 ms, 400–449 ms, 450–499 ms, 500–549 ms, 550–599 ms, 600–649 ms, 650–699 ms, 700–749 ms, 750–799 ms, 800–849 ins, 850–899 ms, 900–949 ms, 950–999 ms, 1000–1049 ins, 1050–1099 ms, and 1100–1049 ms. For each of the sixteen (16) classes, a standard ΔRR probability density histogram is compiled by lumping data together from all the subjects, for example the subjects of the above mentioned MIT-BIH atrial fibrillation/flutter database.

The resulting standard ΔRR probability density histograms are modeled, for example, by the Lorentzian distribution, Gaussian distribution, Student's t-test, or a linear combination of the Lorentzian and Gaussian distribution. In all cases there is excellent superposition of the empirical standard ΔRR probability density histograms and those obtained by any one of the mathematical distributions described above as illustrated in FIGS. 4 to 8. In FIGS. 4–7, the solid line represents the standard ΔRR density histograms and the dotted line is the corresponding standard □RR density histograms obtained by the respective mathematical distributions.

The Lorentzian distribution is defined by the equation:

$$L(x) = \frac{1}{\pi \cdot S}\left(\frac{1}{1+\left(\frac{x}{S}\right)^2}\right)$$

where S is a scaling factor, and x is the ΔRR interval. The Lorenizian distribution is filled to a set of data points of the standard ΔRR probability density histograms using the non-linear least-squares Marquardt-Levenberg algorithm implemented in gnuplot.

The cumulative probability distribution $\Phi_l(x)$ of the Lorentzian distribution is given by the integral:

$$\Phi_l(x) = \int_{-\infty}^{x} L(t)\,dt$$

$$= \int_{-\infty}^{x} \frac{1}{\pi \cdot S}\left(\frac{1}{1+\left(\frac{x}{S}\right)^2}\right) dt$$

$$= \frac{1}{\pi}\arctan\left(\frac{x}{S}\right) + \frac{1}{2}$$

The scaling factor $S_l$ can be expressed by a linear function of the mean RR interval.

$$S_l = a_0 + a_1 * x$$

where $a_0$ and $a_1$ are estimated from the scaling factors determined from the standard ΔRR probability density histograms.

The Gaussian distribution is defined by the equation $$G(x) = \frac{1}{\sqrt{2\pi}\,\sigma}\exp\left(-\frac{(x-\mu)^2}{2\sigma^2}\right),$$

where $\mu$ presents the mean value, and $\sigma$ represents the standard deviation. Here, $\sigma$ corresponds to the standard deviation of the standard $\Delta$RR probability density histograms $\sigma_{std}$. The cumulative probability distribution ($\Phi_g(x)$) of the Gaussian distribution is expressed by the error function ($erf(x)$).

$$\Phi_g(x) = \int_{-\infty}^{x} G(t)\,dt$$
$$= \int_{-\infty}^{x} \frac{1}{\sqrt{2\cdot\pi}\,\sigma}\exp\left(-\frac{t^2}{2\sigma^2}\right)dt$$
$$= \left\{erf\left(\frac{x}{\sqrt{2}\,\sigma_{std}}\right)+1\right\}\Big/2$$

The error function is a special case of the incomplete gamma function, which has an approximate expression. The error function is estimated using the approximation of the incomplete gamma function. As the coefficient of variation is approximately constant during atrial fibrillation, the standard deviation of the Gaussian distribution is also expressed by the linear function:

$$S_l = a_0 + a_1 * x$$

The Student's t-distribution is defined by the equation:

$$T_m(x) = \frac{\Gamma\left(\frac{m+1}{2}\right)}{\Gamma\left(\frac{m}{2}\right)\sqrt{m\cdot\pi}\,S}\left\{1+\frac{1}{m}\left(\frac{x}{S}\right)^2\right\}^{-\frac{m+1}{2}}$$

where m is the degree of freedom. Here, we assume m=6. The mean value of the Student's t-distribution is 0. The variance of the student's t-distribution $\sigma_t^2$ is $$\frac{m}{m-2}\ (m>3).$$

For $m\to\infty$ it approaches the Gaussian distribution. The student's distribution can be modified by a scaling factor S to fit the standard $\Delta$RR probability density histogram. S is determined by the ratio between the standard deviation of the standard $\Delta$RR probability density histogram ($\sigma^2$) and that of the Student's t-distribution.

$$S = \frac{\sigma_{std}}{\sigma_t},$$

where $\sigma_t$ $$\sigma_t = \sqrt{\frac{3}{2}}.$$

By integrating the Student's t-distribution, we obtain a cumulative probability distribution:

$$\Phi_t(x) = \int_{-\infty}^{x} T_6(t)\,dt$$
$$= \int_{-\infty}^{x} \frac{\Gamma\left(\frac{7}{2}\right)}{\Gamma(3)\sqrt{6\pi}\,S}\left\{1+\frac{1}{6}\left(\frac{t}{S}\right)^2\right\}^{-\frac{7}{2}}dt$$
$$= \frac{3}{16}\cos^4\left(\arctan\left(\frac{x}{\sqrt{6}\,S}\right)\right)+\frac{3}{4}\sin\left(\arctan\left(\frac{x}{\sqrt{6}\,S}\right)\right)+\frac{1}{2}$$

where x presents the standard $\Delta$RR probability density histogram. The scaling factor S is expressed by the linear function:

$$S_l = a_0 + a_1 * x$$

The combined probability distribution is defined by a linear combination of the Lorentzian distribution and the Gaussian distribution as defined by:

$$\phi(x) = aL(x) + bG(x)$$
$$= \frac{a}{\pi\cdot S}\frac{1}{1+\left(\frac{x}{S}\right)^2} + \frac{b}{\sqrt{2\pi}\,\sigma}\exp\left(-\frac{x^2}{2\sigma^2}\right)$$

As a corollary the integration of $\phi(x)$ ranging from $-\infty$ to $\infty$ is equal 1.

$$\int_{-\infty}^{\infty}\phi(x)\,dx=1$$

From the above equation we derive that a+b=1. The cumulative probability distribution is defined by the integration of $\phi(x)$ ranging between $-\infty$ and x.

$$\Phi_c(x) = \int_{-\infty}^{x} \phi(t)\,dt$$
$$= \int_{-\infty}^{x}\left\{\frac{a}{\pi S}\frac{1}{1+\left(\frac{t}{S}\right)^2} + \frac{b}{\sqrt{2\pi}\,\sigma_c}\exp\left(-\frac{t^2}{2\sigma_c^2}\right)\right\}dt$$
$$= \frac{a}{\pi S}\int_{-\infty}^{x}\frac{1}{1+\left(\frac{t}{S}\right)^2}dt + \frac{b}{\sqrt{2\pi}\,\sigma_c}\int_{-\infty}^{x}\exp\left(-\frac{t^2}{2\sigma_c^2}\right)dt$$
$$= a\left\{\frac{1}{\pi}\arctan\left(\frac{x}{S}\right)+\frac{1}{2}\right\} + \frac{b}{2}\left\{erf\left(\frac{x}{\sqrt{2}\,\sigma_c}\right)+1\right\}$$
$$= \frac{a}{\pi}\arctan\left(\frac{x}{S}\right) + \frac{b}{2}erf\left(\frac{x}{\sqrt{2}\,\sigma_c}\right) + \frac{1}{2}.$$

The parameters, a (or b), S, and $\sigma_c$ are determined by the curve filling using the nonlinear least-squares Marquardt-Levenberg algorithm implemented in gnuplot. The intermediate value of a, S, and $\sigma_c$ are interpolated from the known values determined from the standard $\Delta$RR probability density histograms.

The resulting modeled histograms are taken to be the standard modeled ΔRR probability density histograms for atrial fibrillation, sorted by the mean RR interval as indicated hereinabove and stored in storage unit 304 (FIG. 3). In other words, a standard ΔRR histogram selector 305 chooses the standard modeled ΔRR probability density histogram corresponding to the class in which the computed mean value of RR intervals (from 204 in FIG. 2) of the block of 100 RR intervals under consideration falls (205 of FIG. 2).

Obviously, it is within the scope of the present invention to construct the standard modeled ΔRR probability density histograms using a different number of consecutive RR intervals, for example 25, 50 or any other number of consecutive RR intervals. It is also within the scope of the present invention to construct the standard modeled ΔRR probability density histograms using mean RR intervals that lie in other ranges, for example 300–399 ms, 400–499 ms, 500–599 ms, etc.

Test ΔRR probability density histograms are constructed (206 of FIG. 2) by a calculator 306 from the data obtained from the patient (test record) through the detector 301. As indicated in the foregoing description, the blocks of 100 successive RR intervals are determined by the counter 302. In the test ΔRR histogram calculator 306 a sequence of 100 RR intervals is centered on each beat in turn, and the relevant test ΔRR probability density histograms are calculated.

In order to test for atrial fibrillation in a test record, a standard cumulative probability distribution is calculated as indicated above depending on the used mathematical distribution, and a test cumulative probability distribution is computed by integrating the area under the curves of the test ΔRR probability density histograms. These standard and test cumulative probability distributions are compared (207 and 208 of FIG. 2) through a comparator 307.

Figure 2:
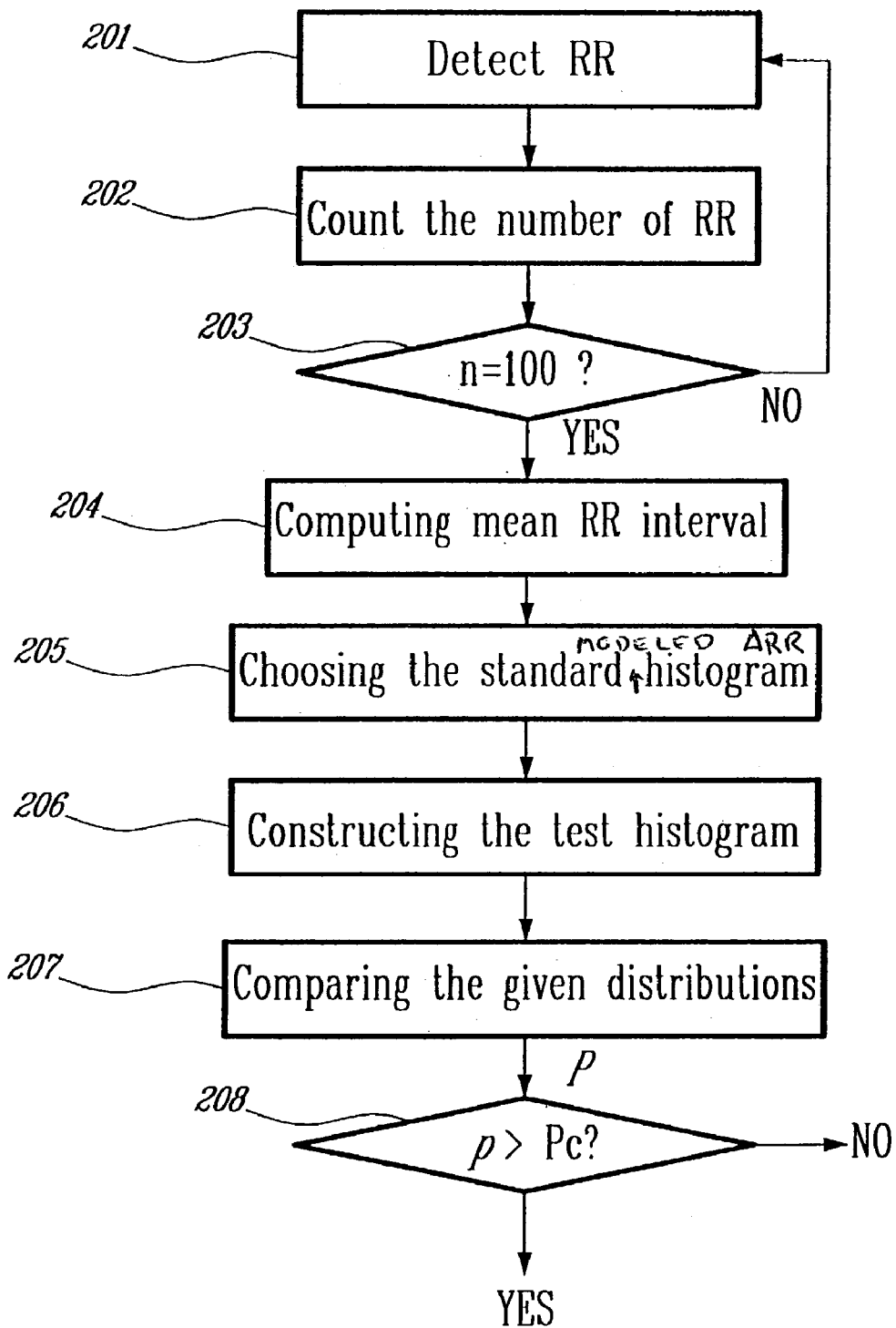
FIG. 2 is a flow chart illustrating an illustrative embodiment of the method according to the present invention, for detecting atrial fibrillation based on RR intervals.

The similarities between the test histograms for a given patient and the standard histograms are evaluated in the comparator 307 using the above mentioned Kolmogorov-Smirnov (KS) test (207 and 208 of FIG. 2).

Referring to FIG. 9, a calculator 901 computes the cumulative probability distribution of the standard modeled ΔRR probability density histograms as described hereinabove depending on the used mathematical distribution. A calculator 902 computes the cumulative probability distribution of the test ΔRR probability density histograms. According to the KS test, one assesses if two given distributions are different from each other. In other words, the greatest vertical distance D (FIG. 10) between the two cumulative probability distributions is measured by a calculator 903 which returns a p value in the following manner:

$$p \equiv Q(\lambda) = 2\sum_{j=1}^{\infty}(-1)^{j-1}e^{-2j^2\lambda^2}$$

where $\lambda = (\sqrt{N_e} + 0.12 + 0.11/\sqrt{N_e})*D$. $N_e =$ $$\frac{N_1 N_2}{N_1 + N_2}.$$

$N_1$ is the number of data points on the standard cumulative probability distribution. $N_2$ is the number of data points in the test cumulative probability distribution. A detector 904 determines whether the p value is greater than a certain, appropriately selected threshold $P_c$, and detection of $p > P_c$ indicates that the cumulative probability distributions are not significantly different from one another. Since the standard ΔRR probability density histograms are representative of atrial fibrillation, a value of $p > P_c$ constitutes a positive identification of atrial fibrillation (or more accurately failure to reject the hypothesis that the test cumulative probability distribution is not atrial fibrillation) (208 in FIG. 2).

The results were assessed by four categories as followed: true positive (TP)—atrial fibrillation is classified as atrial fibrillation; true negative (TN)—non-atrial fibrillation is classified as non-atrial fibrillation; false negative (FN)—atrial fibrillation is classified as non-atrial fibrillation; false positive (FP)—non-atrial fibrillation is classified as atrial fibrillation. Sensitivity and specificity are defined by TP/(TP+FN) and TN/(TN+FP), respectively. The predictive value of a positive test (PV+) and the predictive value of a negative test (PV−) are defined by TP/(TP+FP) and TN/(TN+FN), respectively.

The Kolmogorov-Smirnov test is first applied to the MIT-BIH atrial fibrillation database and $a_0$ and $a_1$ are determined by the linear regression. For the Lorentzian distribution, $a_0 = -58.6216$ and $a_1 = 0.28269$. For the Gaussian distribution, $a_0 = -23.002632$ and $a_1 = 0.343006$. For the Student's t-distribution, $a_0 = -18.78158$ and $a_1 = 0.280063$. FIG. 11 shows the ROC (Receiver Operating Characteristic Curve) of the Kolmogorov-Smirnov test for the MIT-BIH atrial fibrillation database. The accuracy of the Kolmogorov-Smirnov test for the MIT-BIH atrial fibrillation database is summarized in Table 1.

TABLE 1

Accuracy of the Kolmogorov-Smirnov test for the MIT-BIH atrial fibrillation database

| Distribution | $P_c$ | Sensitivity | Specificity | PV+ | PV− |
|---|---|---|---|---|---|
| Lorentzian distribution | 0.0021 | 96.2 | 96.2 | 94.7 | 97.2 |
| Gaussian distribution | 0.0004 | 95.7 | 95.7 | 94.1 | 96.9 |
| Student's t- distribution | 0.0014 | 96.1 | 96.1 | 94.7 | 97.2 |
| Combined distribution | 0.003 | 96.6 | 96.6 | 95.3 | 97.5 |
| Empirical distribution | 0.0039 | 96.5 | 96.5 | 95.2 | 97.5 |

It can be appreciated from the data of Table 1 that the linear combination of the Loretzian distribution and the Gaussian distribution improves the ROC of the Kolmogorov-Smirnov test compared to the ROC of the Kolmogorov-Smirnov test of other single distributions.

FIG. 12 shows the ROC of the Kolmogorov-Smirnov test applied to the 200 series of the MIT-BIH arrhythmia database, which is the test data set. The data is also summarized in Table 2. The linear combination of the Lorentzian distribution and Gaussian distribution (with Pc=0.003) improves the sensitivity compared to the empirical standard histograms, while the other parameters (Specificity, PV+, PV−) are not significantly changed.

TABLE 2

Accuracy of the Kolmogorov-Smirnov test for the MIT-BIH arrhythmia database

| Distribution | $P_c$ | Sensitivity | Specificity | PV+ | PV− |
|---|---|---|---|---|---|
| Lorentzian distribution | 0.0021 | 97.5 | 82.0 | 55.9 | 99.3 |
| Gaussian distribution | 0.0004 | 97.8 | 80.4 | 53.9 | 99.4 |
| Student's t- distribution | 0.0014 | 96.0 | 83.1 | 57.0 | 98.9 |

TABLE 2-continued

Accuracy of the Kolmogorov-Smirnov test
for the MIT-BIH arrhythmia database

| Distribution | $P_c$ | Sensitivity | Specificity | PV+ | PV− |
|---|---|---|---|---|---|
| Combined distribution | 0.003 | 96.0 | 84.7 | 59.5 | 98.9 |
| Empirical distribution | 0.0039 | 93.5 | 84.9 | 59.2 | 98.2 |

Using the probability distribution from the linear combination of the Lorentzian and Gaussian distribution, the Kolmogorov-Smirnov test was also applied to the 100 series of the MIT-BIH arrhythmia database. The results (illustrated in Table 3) are classified, as indicated hereinabove, into four categories: true positive (TP)—atrial fibrillation is classified as atrial fibrillation; true negative (TN)—non-atrial fibrillation is classified as non-atrial fibrillation; false negative (FN)—atrial fibrillation is classified as non-atrial fibrillation; false positive (FP)—non-atrial fibrillation is classified as atrial fibrillation.

As also indicated in the foregoing description, sensitivity and specificity are defined by TP/(TP+FN) and TN/(TN+FP), respectively. The predictive value of a positive test (PV+) and the predictive value of a negative test (PV−) are defined by TP/(TP+FP) and TN/(TN+FN), respectively.

TABLE 3

Accuracy of the Kolmogorov-Smirnov test for
100 series of the MIT-BIH arrhythmia database ($P_c$ = 0.003)

| record | TP | TN | FN | FP |
|---|---|---|---|---|
| 100 | 0 | 2173 | 0 | 0 |
| 101 | 0 | 1765 | 0 | 0 |
| 102 | 0 | 2087 | 0 | 0 |
| 103 | 0 | 1984 | 0 | 0 |
| 104 | 0 | 2129 | 0 | 0 |
| 105 | 0 | 2472 | 0 | 0 |
| 106 | 0 | 1798 | 0 | 129 |
| 107 | 0 | 2037 | 0 | 0 |
| 108 | 0 | 1663 | 0 | 0 |
| 109 | 0 | 2432 | 0 | 0 |
| 111 | 0 | 2024 | 0 | 0 |
| 112 | 0 | 2439 | 0 | 0 |
| 113 | 0 | 1695 | 0 | 0 |
| 114 | 0 | 1779 | 0 | 0 |
| 115 | 0 | 1853 | 0 | 0 |
| 116 | 0 | 2312 | 0 | 0 |
| 117 | 0 | 1435 | 0 | 0 |
| 118 | 0 | 2178 | 0 | 0 |
| 119 | 0 | 1858 | 0 | 29 |
| 121 | 0 | 1763 | 0 | 0 |
| 122 | 0 | 2376 | 0 | 0 |
| 123 | 0 | 1418 | 0 | 0 |
| 124 | 0 | 1519 | 0 | 0 |
| total | 0 | 45189 | 0 | 158 |

Using the method described herein, table 3 shows that subject 106, characterized as having premature ventricular contractions, emerges as false positive. It is known that frequent premature ventricular contractions often disturb the detection of atrial fibrillation. FIG. 13 shows that both specificity and sensitivity are improved when premature ventricular contractions (PVC) are removed from the 200 series of the MIT-BIH arrhythmia database and the Kolmogorov-Smirnov test is applied to the combined Lorentzian and Gaussian probability distribution.

It will appear to those of ordinary skill in the art that the method of FIG. 2 and the system of FIG. 3 can be implemented through a properly programmed computer.

It is also within the scope of the present invention to use signals other than the RR intervals, histograms other than ΔRR probability density histograms, tests other than the KS test, and series of ΔRRs other than 100, and that other methods besides the Komogorov-Smirnov test can be used to compare test histograms with the standard histograms.

Although the present invention has been described hereinabove by way of illustrative embodiment thereof, this embodiment can be modified at will, within the scope of the appended claims, without departing from the spirit and nature of the subject invention.

The invention claimed is:

1. A method for detecting cardiac arrhythmia of a patient, comprising:
    detecting RR intervals of the patient wherein each RR interval is an interval between two heart beats;
    constructing standard probability density histograms of ΔRRs collected during cardiac arrhythmia of a plurality of subjects, wherein ΔRR is a difference between two successive RR intervals;
    modeling the standard probability density histograms of ΔRRs by means of a suitable probability distribution calculated through at least one mathematical formulae;
    constructing test probability density histograms of ΔRRs of the patient from the detected RR intervals of said patient; and
    comparing the standard modeled histograms and the test histograms to detect whether the patient suffers from cardiac arrhythmia,
    wherein comparing the standard modeled histograms and the test histograms to detect whether the patient suffers from cardiac arrhythmia comprises performing a Kolmogorov-Smirnov test, said method further comprising eliminating premature ventricular contractions prior to performing the Kolmogorov-Smirnov test.

2. A computer readable medium for encoding instructions for detecting cardiac arrhythmia of a patient, comprising:
    instructions encoded on a computer readable medium for detecting RR intervals of a patient wherein each RR interval is an interval between two heart beats;
    instructions encoded on the computer readable medium for constructing standard probability density histograms of ΔRRs collected during cardiac arrhythmia of a plurality of subjects, wherein ΔRR is a difference between two successive RR intervals;
    instructions encoded on the computer readable medium for modeling the standard probability density histograms of ΔRRs by means of a suitable probability distribution calculated through at least one mathematical formulae;
    instructions encoded on the computer readable medium for constructing test probability density histograms of ΔRRs of the patient from the detected RR intervals of said patient; and
    instructions encoded on the computer readable medium for comparing the standard modeled histograms and the test histograms to detect whether the patient suffers from cardiac arrhythmia,
    wherein the instructions encoded on the computer readable medium for comparing the standard modeled histograms and the test histograms to detect whether the patient suffers from cardiac arrhythmia comprises instructions for executing a Kolmogorov-Smirnov test, and executing instructions for eliminating premature ventricular contractions prior to performing the Kolmogorov-Smirnov test.

3. An apparatus for detecting cardiac arrhythmia of a patient, comprising:

means for detecting RR intervals of a patient wherein each RR interval is an interval between two heart beats;

means for constructing standard probability density histograms of ΔRRs collected during cardiac arrhythmia of a plurality of subjects, wherein ΔRR is a difference between two successive RR intervals;

means for modeling the standard probability density histograms of ΔRRs by means of a suitable probability distribution calculated through at least one mathematical formulae;

means for constructing test probability density histograms of ΔRRs of the patient from the detected RR intervals of said patient; and means for comparing the standard modeled histograms and the test histograms to detect whether the patient suffers from cardiac arrhythmia, wherein comparing the standard modeled histograms and the test histograms to detect whether the patient suffers from cardiac arrhythmia comprises performing a Kolmogorov-Smirnov test, and wherein said apparatus also includes means for eliminating premature ventricular contractions prior to performing the Kolmogorov-Smirnov test.

* * * * *